United States Patent [19]
Boute

[11] Patent Number: 5,534,016
[45] Date of Patent: Jul. 9, 1996

[54] DUAL CHAMBER PACING SYSTEM AND METHOD UTILIZING DETECTION OF VENTRICULAR FUSION FOR ADJUSTMENT OF THE ATRIAL-VENTRICULAR DELAY AS THERAPY FOR HYPERTROPHIC OBSTRUCTIVE CARDIOMYOPATHY

[75] Inventor: Willem Boute, Dieren, Netherlands

[73] Assignee: Vitatron Medical, B.V., Dieren, Netherlands

[21] Appl. No.: 395,372

[22] Filed: Feb. 21, 1995

[51] Int. Cl.$^6$ .................................................. A61N 1/362
[52] U.S. Cl. ............................................................ 607/9
[58] Field of Search .................................. 607/9, 26, 27, 607/28

[56] References Cited

U.S. PATENT DOCUMENTS

| | | | |
|---|---|---|---|
| 4,969,464 | 11/1990 | Callaghan et al. | 607/28 |
| 5,334,220 | 8/1994 | Sholder | 607/9 |
| 5,340,361 | 8/1994 | Sholder | 607/24 |

OTHER PUBLICATIONS

McDonald, Kenneth et al., "Permanent Pacing As Treatment For Hypertrophic Cardiomyopathy," The American Journal Of Cardiology, vol. 68, Jul. 1, 1991, pp. 108–110.

Jeanrenaud, Xavier et al., "Effects of Dual–Chamber Pacing In Hypertrophic Obstructive Cardiomyopathy," The Lancet, vol. 339, May 30, 1992, pp. 1318–1323.

McAreavey, Dorothea et al., "Altered Cardiac Hemodynamic and Electrical State in Normal Sinus Rhythm After Chronic Dual–Chamber Pacing For Relief of Left Ventricular Outflow Obstruction in Hypertrophic Cardiomyopathy," American Journal of Cardiology, vol. 7, Sep. 1992, pp. 651–656.

Seidelin, P. H., "Effects of Dual–Chamber Pacing in Hypertrophic Cardiomyopathy Without Obstruction," The Lancet, vol. 340, Aug. 8, 1992, pp. 369–370.

Boute, W., et al., "Morphology of Endocardial T–Waves of Fusion Beats," Pace, vol. 11, Nov. 1988, Part II., pp. 1693–1697.

Parsonnet, et al., "The Development of an Intracardiac Dipolar Catheter Electrode For the Treatment of Complete Heart Block," Surgical Forum.

*Primary Examiner*—William E. Kamm
*Assistant Examiner*—Scott M. Getzow
*Attorney, Agent, or Firm*—Woodcock Washburn Kurtz Mackiewicz & Norris

[57] ABSTRACT

A dual chamber pacemaker for providing ventricular pace pulses synchronized with atrial senses or paces, and having specific control for optimizing the AV escape interval and resultant AV delay for purposes of therapy for a patient with hypertrophic obstructive cardiomyopathy (HOCM). The pacemaker has an algorithm for varying the AV escape interval and detecting when the AV delay is lengthened to the point of evoking a fusion beat, thereby providing an accurate indication of a patient's underlying PR interval without significant loss of pacing capture. By monitoring T-wave detection and drop in amplitude of the evoked T-wave, an algorithm is enabled for optimizing the pacemaker AV delay within a range of values just less than the longest value for obtaining pre-excitation by the delivered pace pulse.

18 Claims, 6 Drawing Sheets

DUAL CHAMBER PACING SYSTEM AND METHOD UTILIZING DETECTION OF VENTRICULAR FUSION FOR ADJUSTMENT OF THE ATRIAL-VENTRICULAR DELAY AS THERAPY FOR HYPERTROPHIC OBSTRUCTIVE CARDIOMYOPATHY

BACKGROUND OF THE INVENTION

This invention relates to cardiac pacing systems and methods generally and, in particular, to dual chamber cardiac pacing systems and methods for delivering ventricular pacing pulses synchronized to atrial signals so as to benefit patients with Hypertrophic Obstructive Cardiomyopathy.

Hypertrophic Obstructive Cardiomyopathy (HOCM) is characterized by a narrowed left ventricular outflow tract (LVOT), which causes a significant increase in the subaortic pressure gradient. The narrowed LVOT is caused by an increased thickness of the interventricular septum which obstructs blood flow during systole, or at the time of cardiac output.

Symptomatic improvement of patients with HOCM can be obtained in some cases with the use of standard pharmacotherapy. However, drugs in use for this therapy have disadvantages which have been cited in the literature. Likewise, surgical intervention, e.g., septal myectomy or mitral valve replacement, is another optional treatment. However, such surgical treatments carry a significant operative mortality and have not been shown to alter the natural history of the disease. See, "Permanent Pacing As Treatment For Hypertrophic Cardiomyopathy," by Kenneth M. McDonald et al., *American Journal of Cardiology*, Vol. 68, pp. 108–110, July 1991.

The value of dual chamber cardiac pacing and treatment of patients suffering from HOCM has been recognized in the literature. Modern multiple-mode, dual-chamber cardiac pacemakers are designed to maintain AV synchrony for damaged or diseased hearts that are unable to do so on their own. For example, a DDD pacemaker has electrical connections to both the atrium and the ventricle, senses electrical signals in both chambers of the patient's heart, and delivers atrial pacing stimuli in the absence of signals indicative of natural atrial contractions, and ventricular pacing stimuli in the absence of signals indicative of natural ventricular contractions. Such a dual chamber pacemaker maintains the AV synchrony of the heart by delivering ventricular pace pulses at a controlled AV interval following each atrial event.

Studies have indicated that patients suffering from HOCM may benefit from a specific mode of dual chamber pacing wherein a ventricular pace pulse is delivered in timed synchrony with the sensed or paced atrial depolarization. Pacing the right ventricular apex before spontaneous atrioventricular conduction activates the left ventricle is understood to alter the ventricular septal activation pattern. This reduces leftward motion of the septum, thereby reducing the LVOT obstruction and subaortic pressure gradient.

The literature uniformly acknowledges the potential advantages of synchronized A-V pacing for HOCM patients, stressing the importance of achieving ventricular capture. Causing "complete ventricular capture" is important to obtain the above-described septal movement, while selecting the longest AV delay that results in complete ventricular capture is important in order to maximize the atrial contribution to ventricular filling. See U.S. application Ser. No. 08/214,933, filed Mar. 17, 1994, Method and Apparatus For Dual Chamber Cardiac Pacing, assigned to Medtronic, Inc., and the literature articles referenced therein. The delivered pace pulse should provide "pre-excitation," i.e., depolarization of the ventricular apex before the septum. This altered pattern of septal contraction, as well as optimal left ventricular filling, is generally recognized as being important to this mode of pacemaker treatment. Further, it appears to be established that such synchronized AV pacing provides HOCM patients a long term benefit, i.e., the benefit remains even after cessation of pacing, since such AV pacing causes a reduction in the obstruction of the LVOT which persists in sinus rhythm after cessation of pacing.

The literature suggests that the AV escape interval should be set at the longest duration that maintains ventricular capture at different exercise levels. See the above-cited McDonald article. It has been suggested that the AV escape interval which allows for maximal pre-excitation of the ventricle by the pacing pulse can be selected by determining the AV escape interval that produces the widest paced QRS complex duration. See "Impact of Dual Chamber Permanent Pacing in Patients With Obstructive Hypertrophic Cardiomyopathy With Symptoms Refractory to Verapamil and β-Adrenergic Blocker Therapy," by Fananapazir et al., *Circulation*, Vol. 8, No. 6, June 1992, pp. 2149–2161.

In the referenced U.S. application assigned to Medtronic, Inc., the pacemaker periodically checks to determine a value of intrinsic AV conduction time (AVC) and subtracts therefrom a ventricular sense offset interval (VSO) to get the AV escape interval. After a waveform of the ventricular depolarization resulting from complete capture is noted and recorded for comparison, the AV escape interval is set to a lengthened value, resulting in one or more ventricular sense events. The value of AVC is determined as the time difference between the atrial event and the sensed R-wave. Following this, the pacemaker AV escape interval is reduced further until the pacemaker finds an R wave with a waveform that indicates good capture. The difference between AVC and the capture valve of AV is USO, and the pacemaker thereafter sets AV=AVC−VSO.

The prior art techniques for synchronous pacing of HOCM patients recognize the necessity to periodically evaluate the AV delay, or AV escape interval. The patient's spontaneous atrio-ventricular conduction time generally will change with heart rate, i.e., from rest to exercise. Moreover, simultaneous drug treatment such as beta blockers may also modify AV conduction time and require renewed evaluation of the AV delay. If the AV delay is adjusted to a value which is too short, in order to ensure complete ventricular capture, the atrial contribution to ventricular filling is compromised. However, if the AV escape interval is adjusted to too great a value, ventricular capture is compromised, and there may be episodes of no ventricular pacing or the ventricular pace may not contribute the best possible reduction of the LVOT obstruction. Accordingly, it is important in this therapy to be able to continuously adjust the AV escape interval to reliably position it to a value safely short of the intrinsic AV conduction time, while advantageously avoiding episodes of natural heartbeats where the AV delay is too long to provide the benefit of delivered ventricular pace pulses.

SUMMARY OF THE INVENTION

This invention provides an apparatus and method utilizing ventricular fusion beat detection as the basis for an automatic AV delay algorithm for dual chamber pacing therapy in patients with HOCM. When the AV interval of a dual chamber pacemaker is set to substantially the same value as the natural conduction time, such that the ventricular pace pulse is generated at about the same time that the R-wave naturally occurs, there results a condition known as "fusion." This condition is not necessarily harmful, but has been viewed as undesired because the energy of the pace pulse is wasted since the cardiac tissue is refractory and does not respond to the pace pulse. When fusion occurs, the resulting R-wave morphology is different from the morphology either of a natural QRS wave or one that results from full capture by the delivered pace pulse. This change in morphology includes a change in the frequency content of the R-wave and the T-wave. Further, the amplitude of the T-wave evoked by the pace pulse decreases substantially as fusion is achieved; the amplitude of the T-wave following natural ventricular depolarization (VS) is too low to be sensed by the T-wave sense amplifier. Thus, if successive ventricular stimulus pulses are delivered with AV delays which successively increase toward the intrinsic AV interval, a change in the T-wave morphology and, specifically, a decrease in the T-wave amplitude, can be observed as the AV interval approaches a value that produces fusion beats. It is thus possible to provide a pacemaker which monitors the T-wave response for an indication of when and as the AV delay approaches the value at which fusion occurs ($AV_{fus}$), which generally corresponds to the intrinsic PR interval (AVC) minus an offset. The pacemaker utilizes this information for adjusting the pacemaker AV escape interval ($AV_{esc}$) to deliver ventricular pace pulses at a time within a small range of values just before fusion would occur. Since a ventricular pace pulse that results in a fusion beat does not provide full capture, it is desired to use the onset of fusion as the dynamic upper limit of the range of $AV_{esc}$ used by the pacemaker.

In the pacemaker apparatus and method of this invention, the pacemaker uses an algorithm which adjusts the AV delay within a range having an upper limit of $AV_{fus}$, so as to maximize complete ventricular capture. In order to adapt $AV_{esc}$ so as to maintain optimal pre-excitation, the pacemaker is programmed to increase the AV delay until the onset of ventricular fusion is detected. In one embodiment, following detection of ventricular fusion or onset of fusion, $AV_{esc}$ is immediately shortened to a value which assures complete ventricular capture, following which $AV_{esc}$ is increased stepwise every beat until ventricular fusion is again detected. By using ventricular fusion as the control variable for adjusting $AV_{esc}$, there is provided a continuously automatic adjustment of $AV_{esc}$, capable of maintaining $AV_{esc}$ within a small dynamic range just less than the intrinsic AV conduction, with continuous capture by pace pulses except for the instance of quasi-complete or semi-complete capture at the onset of fusion. In this arrangement, the pacemaker of this invention avoids the necessity of incurring sensed ventricular events or even multiple fusion beats, while providing an optimum AV delay for ventricular filling, thereby maximizing benefit of the pacing therapy for the HOCM patient.

In a preferred embodiment, the driving variable for adjusting $AV_{esc}$ is T-wave detection. The apparatus of this invention monitors T-wave amplitude, and determines when such T-wave amplitude drops by a sufficient absolute or relative amount to indicate failure of T-wave detection, indicating fusion or onset of fusion. In response, the pacemaker first institutes an aggressive decrease in $AV_{esc}$, e.g., 20 ms, and thereafter follows a program for incrementing $AV_{esc}$ during successive pacemaker cycles, so as to return $AV_{esc}$ toward the prior observed value of $AV_{fus}$. Preferably, as $AV_{esc}$ approaches the prior determined value of $AV_{fus}$, $AV_{esc}$ is increased by even shorter increments, thereby maximizing the number of pace pulses delivered just prior to the timing out of the intrinsic AV conduction interval.

DETAILED DESCRIPTION OF THE PREFERRED EMBODIMENTS

Figure 1:
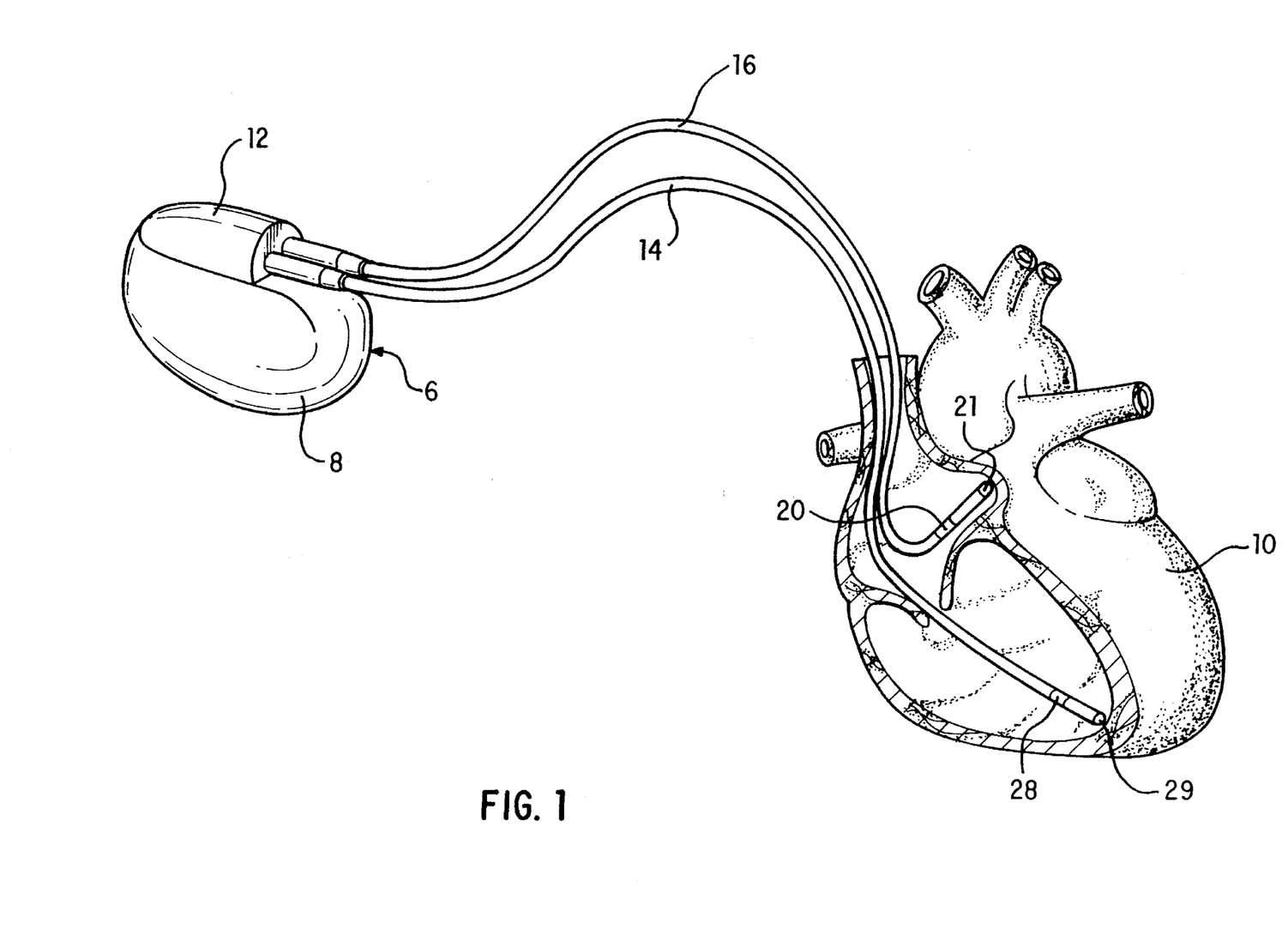
FIG. 1 is a perspective representation of the pacemaker system of this invention showing an implantable pacemaker connected to a patient's heart.

FIG. 1 illustrates the external configuration of a dual chamber pacemaker 6, which is provided with a hermetically sealed enclosure 8, typically fabricated of biocompatible metal such as titanium. Mounted to the top of the enclosure 8 is a connector block assembly 12, which receives electrical connectors located on the proximal ends of leads 14 and 16. Lead 16 is an atrial pacing lead, carrying two electrodes 20 and 21. Electrodes 20 and 21 are used both to sense atrial depolarizations and to deliver atrial pacing pulses. Atrial pacing pulses may be delivered between electrode 20 and electrode 21 or between electrode 21 and the housing 8 of the pacemaker 6. Sensing of atrial depolarizations may occur between electrode 20 and electrode 21 or between either of electrode 20 and 21 and the housing 8 of the pacemaker 6.

Similarly, lead 14 represents a ventricular bipolar pacing lead, carrying two electrodes 28 and 29. As discussed above in conjunction with atrial lead 16, electrodes 28 and 29 are used to sense and pace the ventricle. Ventricular pacing may be accomplished between electrodes 29 and 28 or between electrode 29 and the conductive housing 8 of pacemaker 6. Sensing of ventricular signals, including depolarizations (QRS-waves) and repolarizations (T-waves) may be accomplished between electrodes 29 and 28 or between either of electrodes 29 and 28 and the housing 8 of the pacemaker 6.

As discussed in the present application, the preferred embodiments of the pacemaker 6 operate in a DDD or DDDR pacing mode, wherein pacing pulses are delivered to both atrium and ventricle and wherein atrial and ventricular depolarizations are both effective to inhibit delivery of the next scheduled pacing pulse in the chamber in which they are detected. DDDR may be indicated for patients that have drug-induced chronotropic incompetence. While the present invention is believed optimally practiced in a pacemaker operating in DDD or DDDR pacing mode, in some patients there may also be a benefit to operating the device in VDD or DVI mode, which provides ventricular pacing pulses synchronized only to sensed atrial depolarizations or only delivered to atrial pacing pulses, respectively, depending upon the specific underlying heart condition of the patient. However, DDD or DDDR mode is expected to be the mode most widely used to practice the present invention.

Figure 2:
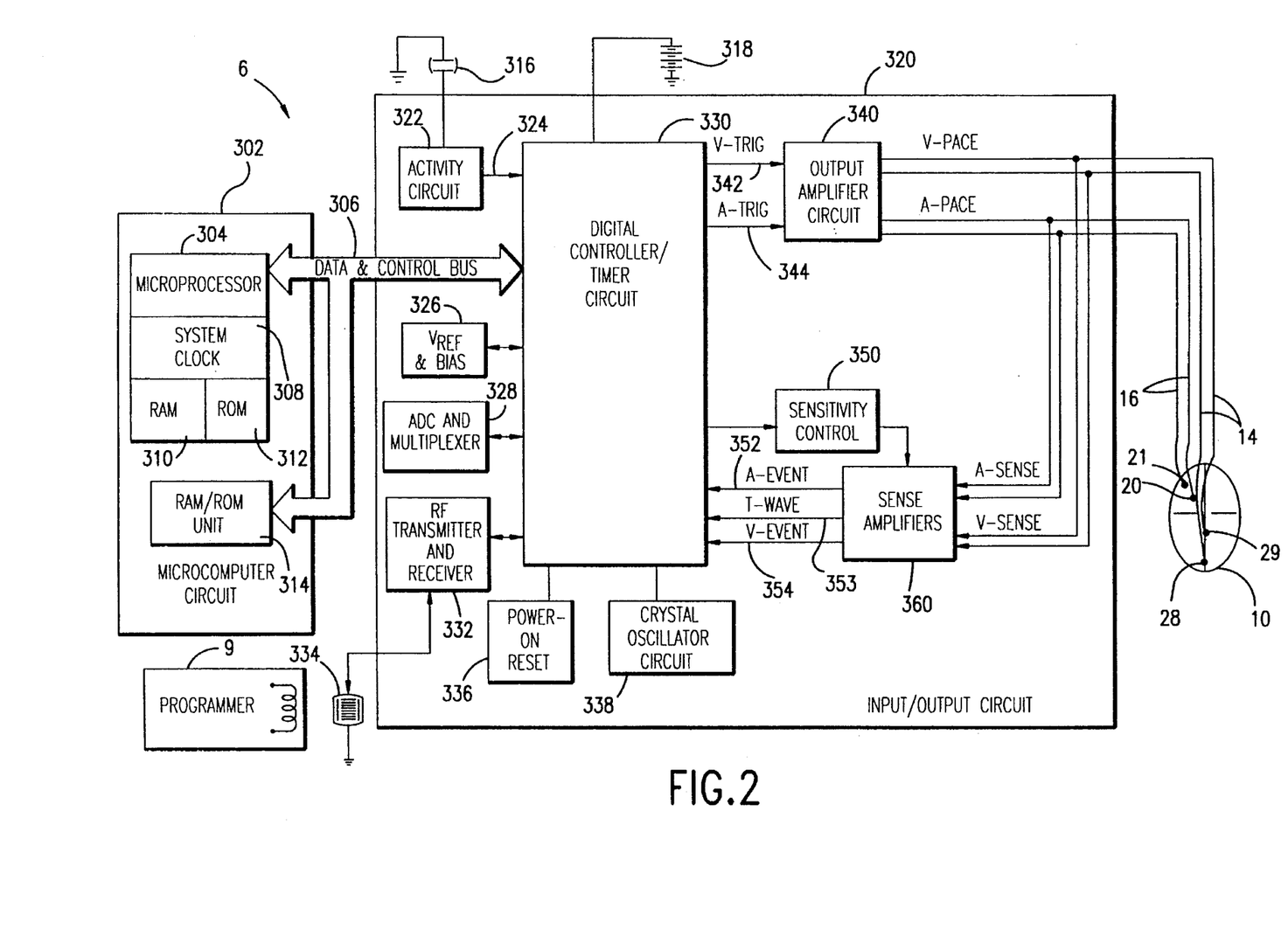
FIG. 2 is a block diagram of the primary functional components of the pacemaker system and method of this invention.

FIG. 2 is a block functional diagram of the pacemaker illustrated in FIG. 1, as connected to a human heart 10. The circuitry illustrated is all located within the conductive housing or can 8 of the pacemaker, as illustrated in FIG. 1, and the bipolar leads 14 and 16 are illustrated schematically as coupled directly to the circuit. However, of course, in the actual device they would be coupled by means of removable electrical connectors inserted in the connector block 12, as illustrated in FIG. 1.

The pacemaker is divided generally into a microcomputer circuit 302 and a pacing circuit 320. A pulse generator circuit 340 includes a ventricular pulse generator circuit coupled to the heart 10 by means of electrodes 29 and 28 on lead 14, as well as an atrial pulse generator circuit coupled to the heart 10 by means of atrial electrodes 20 and 21, located on lead 16. Similarly, pacing circuit 320 includes atrial and ventricular sense amplifiers in sense amplifier circuit 360, coupled to the atrium and ventricle by means of leads 14 and 16 as well. The ventricular sense amplifier provides for separate detection and identification of QRS-wave and T-wave signals, in a known manner. The output circuit 340 and sense amplifier circuit 360 may contain pulse generators and sense amplifiers corresponding to any of those presently employed in commercially marketed cardiac pacemakers. Control of timing and other functions within the pacemaker circuit is provided by digital controller/timer circuit 300, which includes a set of timers and associated logic. Digital controller/timer circuit 330 defines the basic pacing interval of the device, which may take the form of an A-A escape interval initiated on atrial sensing or pacing and triggering atrial pacing at the expiration thereof, or may take the form of a V-V escape interval, initiated on ventricular sensing or pacing and triggering ventricular pulse pacing at the expiration thereof. Digital controller/timer circuit 330 similarly defines the A-V escape interval, $AV_{esc}$, discussed in detail below. The specific values of the intervals defined are controlled by the microcomputer circuit 302 by means of data and control bus 306. Sensed atrial depolarizations are communicated to the digital controller/timer circuit 330 on A event line 352; ventricular depolarizations (QRS-waves) are communicated to the digital controller/timer circuit 330 on V event line 354; and ventricular repolarizations (T-waves) are connected to circuit 330 on T-wave line 353. In order to trigger generation of a ventricular pacing pulse, digital controller/timer circuit 330 generates a trigger signal on V trig line 342. Similarly, in order to trigger an atrial pacing pulse, digital controller/timer circuit 330 generates a trigger pulse on a trig line 344.

Digital controller/timer circuit 330 also defines time intervals for controlling operation of the sense amplifiers in sense amplifier circuit 360. Typically, digital controller/timer circuit 330 will define an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 330 will also define an atrial refractory period during which atrial sensing is disabled, this refractory period extending from the beginning of the A-V escape interval following either a sensed or paced atrial depolarization, and extending until a predetermined time following sensing of a ventricular depolarization or delivery of a ventricular pacing pulse. Digital controller/timer circuit 330 similarly defines a ventricular refractory period following ventricular sensing or delivery of a ventricular pacing pulse, which is typically shorter than the portion of the atrial refractory period following ventricular sensing or pacing. Digital controller/timer circuit 330 also controls sensitivity settings of the sense amplifiers 360 by means of sensitivity control 350. This sensitivity control may be utilized to distinguish QRS-waves and T-waves. See U.S. Pat. No. 4,665,919, incorporated herein by reference.

In the embodiment illustrated in FIG. 2, the pacemaker is provided with a piezo electric sensor 316 which is intended to monitor patient activity, in order to allow provision of rate responsive pacing, such that the defined pacing rate (A-A escape interval or V-V escape interval) increases with increased demand for oxygenated blood. Sensor 316 generates electrical signals in response to sensed physical activity which are processed by activity circuit 322 and provided to digital controller/timer circuit 330. Activity circuit 332 and associated sensor 316 may correspond to the circuitry disclosed in U.S. Pat. No. 5,052,388, issued to Betzold et al., and U.S. Pat. No. 4,428,378, issued to Anderson et al. incorporated herein by reference in their entireties. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Transmission to and from the external programmer 9 illustrated in FIG. 2 is accomplished by means of antenna 334 and associated RF transmitter and receiver 322, which serves both to demodulate received downlink telemetry and to transmit uplink telemetry. Crystal oscillator circuit 338 provides the basic timing clock for the circuit, while battery 318 provides power. Power on reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexor 328, power on reset circuit 336 and crystal oscillator circuit 338 may correspond to any of those presently used in current marketed implantable cardiac pacemakers.

Figure 3A:
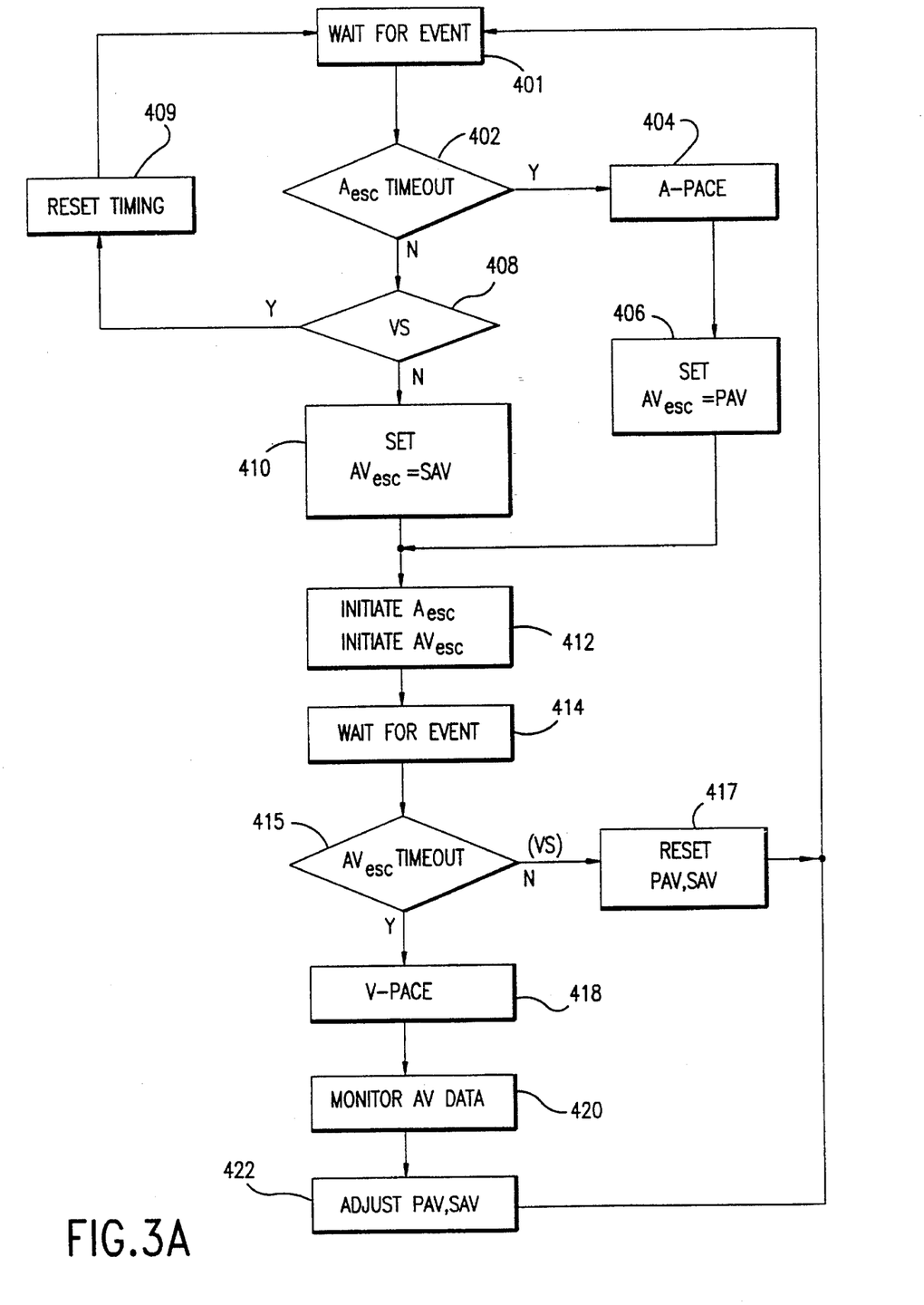
FIG. 3A is a generalized flow diagram illustrating steps taken in synchronous pacing in accordance with this invention.

Microcomputer circuit 302 controls the operational functions of digital controller/timer 330, specifying which timing intervals are employed, and controlling the duration of the various timing intervals, via data and control bus 306. Microcomputer circuit 302 contains a microprocessor 304 and associated system clock 308 and on processor RAM circuits 310 and 312, respectively. In addition, microcomputer circuit 302 includes a separate RAM/ROM chip 314. Microprocessor 304 is interrupt driven, operating in a reduced power consumption mode normally, and awakened in response to defined interrupt events, which may include delivery of atrial and ventricular pacing pulses as well as sensed atrial and ventricular depolarizations. In addition, if the device operates as a rate responsive pacemaker, a timed interrupt, e.g., every cycle or every two seconds, may be provided in order to allow the microprocessor to analyze the sensor data and update the basic rate interval (A-A or V-V) of the device. In addition, in a preferred embodiment of the invention, the microprocessor 304 may also serve to define variable A-V escape intervals and atrial and ventricular refractory periods which may also decrease in duration along with decreases in duration of the basic rate interval. Specifically, the microprocessor is used to carry out the routines illustrated in FIGS. 3 and 4.

The illustrated circuitry of FIG. 2 is merely exemplary, and corresponds to the general functional organization of most microprocessor controlled cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microprocessor circuit 302. However, the present invention many also be usefully practiced by means of a full custom integrated circuit, or any combination of hardware and software.

Referring now to FIG. 3, there is shown a generalized flow diagram of the steps taken by the pacemaker of this invention in performing the method of adjusting $AV_{esc}$ for optimal synchronous pacing of the ventricle to provide HOCM therapy. The steps of this flow diagram are suitably carried out by microcomputer circuit 302. This is a simplified flow diagram setting forth the steps pertinent to controlling $AV_{esc}$ for purposes of HOCM therapy, and does not include many other steps and responses that occur during each cycle of a typical dual chamber pacemaker. The illustrated logic of FIG. 3 recognizes that the intrinsic AV conduction time following an atrial pace pulse is greater than following a sensed atrial depolarization, by an amount described as "atrial sense offset", or ASO in referenced U.S. application Ser. No. 08/214,933. The $AV_{esc}$ following an atrial pace is defined as PAV; the $AV_{esc}$ following an atrial sense is defined as SAV; and PAV=SAV+ASO. While the invention is illustrated in terms of generating separate values of SAV and PAV, the invention as claimed is not so limited.

At block 401, the routine of FIG. 3 is waiting for what is expected to be an atrial event. When an event occurs, the routine goes to block 402 and determines whether there has been timeout of the atrial escape interval, $A_{esc}$. If yes, this indicates that an atrial pace (AP) should be delivered, and this is done at block 404. Then, at block 406, the routine sets $AV_{esc}$ to PAV, and goes to 412 to initiate timeout of $AV_{esc}$. Returning to 402, if there has been no timeout of $A_{esc}$, the pacemaker proceeds to 408, and determines whether there has been an early ventricular sense (VS). If yes, the routine branches to block 409 and resets the timing appropriately, whereafter it returns to block 401. However, as would normally be the case, if at 408 the event is not a VS, meaning that it has been an atrial sense (AS), the routine proceeds to block 410 and sets $AV_{esc}$ to the current value of SAV. Following this, the routine goes to 412 and initiates timeout of the atrial escape interval ($AV_{esc}$), and timeout of the AV escape interval, $AV_{esc}$ (either SAV or PAV). Then, at 414, the pacer waits for the next event, normally a ventricular event.

At 415, the pacemaker responds to an event by first determining whether the event was a timeout of $AV_{esc}$. If no, meaning that there was a ventricular sense, the pacemaker proceeds to block 417 and resets PAV and SAV to a shorter value which ensures capture by the next ventricular pace pulse. For example, each of these values can be decremented by 50 ms, to ensure that succeeding timeouts of $AV_{esc}$ occur early enough to ensure ventricular capture. It is to be noted, however, that the algorithm discussed below are designed to avoid an occurrence of VS, such that the pacemaker should rarely take this path.

If at 415 there has been a timeout of $AV_{esc}$, then the pacemaker proceeds to block 418 and delivers a V pace. After this, the routine proceeds to block 420 and monitors AV data. As discussed above, this data is preferably T-wave amplitude, or T-wave morphology. With this dam in hand, the pacemaker adjusts the values of PAV and SAV at 422, in accordance with a predetermined algorithm for maximizing $AV_{esc}$ so as to optimize resultant pre-excitation. Following this, the routine returns to block 401 and waits for the next atrial or ventricular (e.g., PVC) event.

Note that while the preferred embodiment comprises monitoring AV data and adjusting $AV_{esc}$ each pacemaker cycle, these steps could be taken on some other periodic or programmed basis, within the scope of the invention.

Figure 3B:
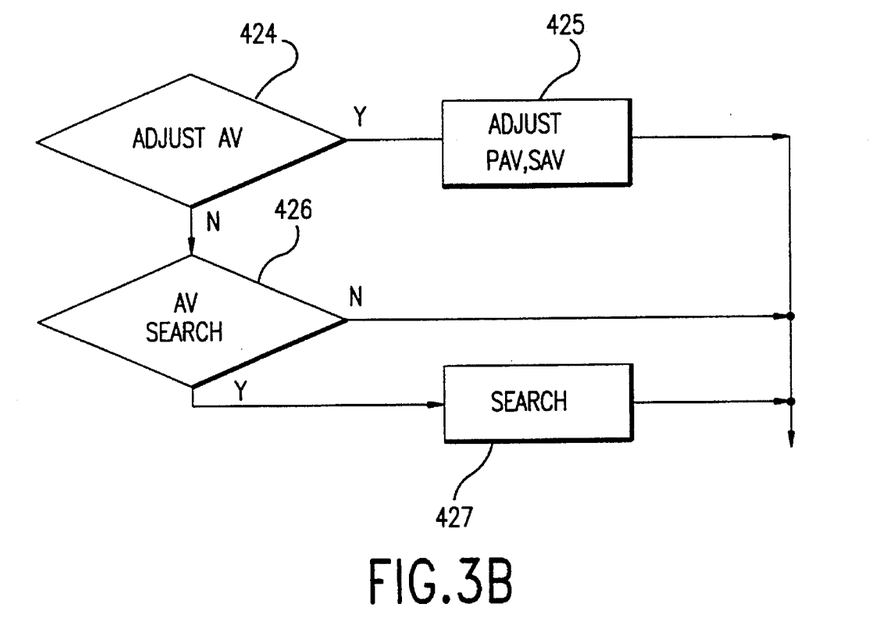
FIG. 3B is a simplified flow diagram illustrating a search step.

Referring now to FIG. 3B, there is shown a simplified flow diagram of steps taken corresponding to block 422, which includes a search, or scan in order to move $AV_{esc}$ toward the value corresponding to fusion. At block 424, the pacemaker determines, based upon the monitored data, whether AV should be adjusted. If yes, the routine adjusts PAV and SAV, as shown in 425. However, if no adjustment is in order, the routine goes to 426, and determines whether the pacemaker is programmed to conduct an AV search, or scan. If no, then the routine exits. However, if it is programmed to search, it goes to block 427, and adjusts $AV_{esc}$ in accordance with a pre-determined search routine. The search routine is designed to take $AV_{esc}$ toward the fusion value. The search routine may be any programed routine, e.g., one of the routines illustrated in FIGS. 5B, 5C, 5D, and 5E.

Figure 3C:
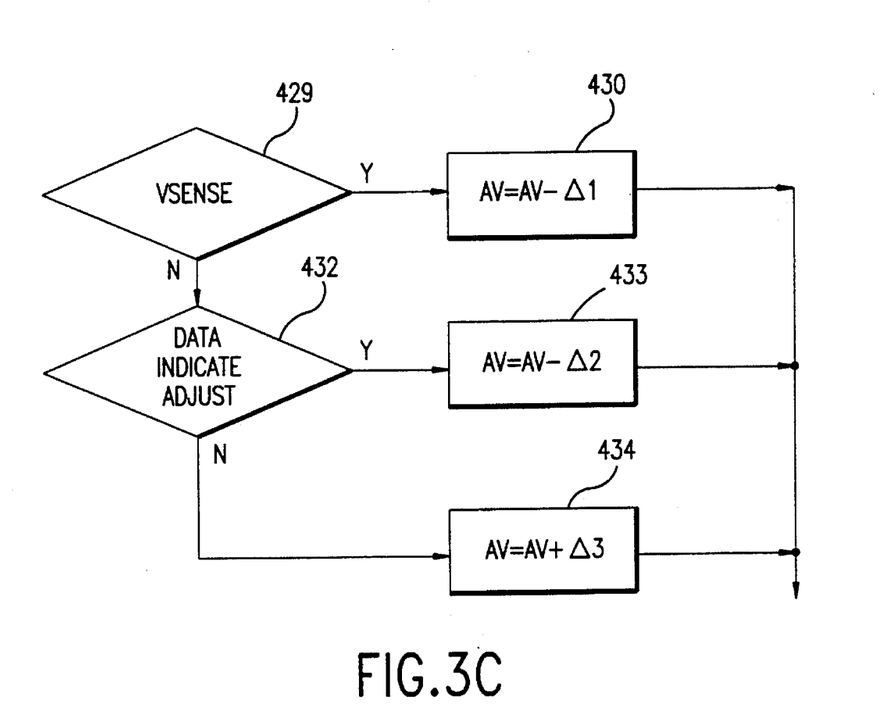
FIG. 3C is a simplified flow diagram illustrating a specific routine for searching and adjusting $AV_{esc}$.

Referring to FIG. 3C, there is shown a simplified flow diagram summarizing a simple routine for adjusting AV as well as scanning or searching. At 429, the routine determines whether there has been a V sense. If yes, then the routine branches to 430 and decrements AV by $\Delta1$, e.g. 25 or 50 ms. However, if there has bee no V sense, the routine goes to 432 and determines whether the monitored data indicate that an adjustment should be made. If yes, then the routine goes to 433 and decrements AV by $\Delta2$, which may be the same as or smaller than $\Delta1$. If, at 432, the data do not indicate an adjust, then the routine goes to block 434 to execute a simple scan step, i.e., incrementing AV by $\Delta3$, where $\Delta3$ is preferably a small value such as 5 ms.

Figure 4:
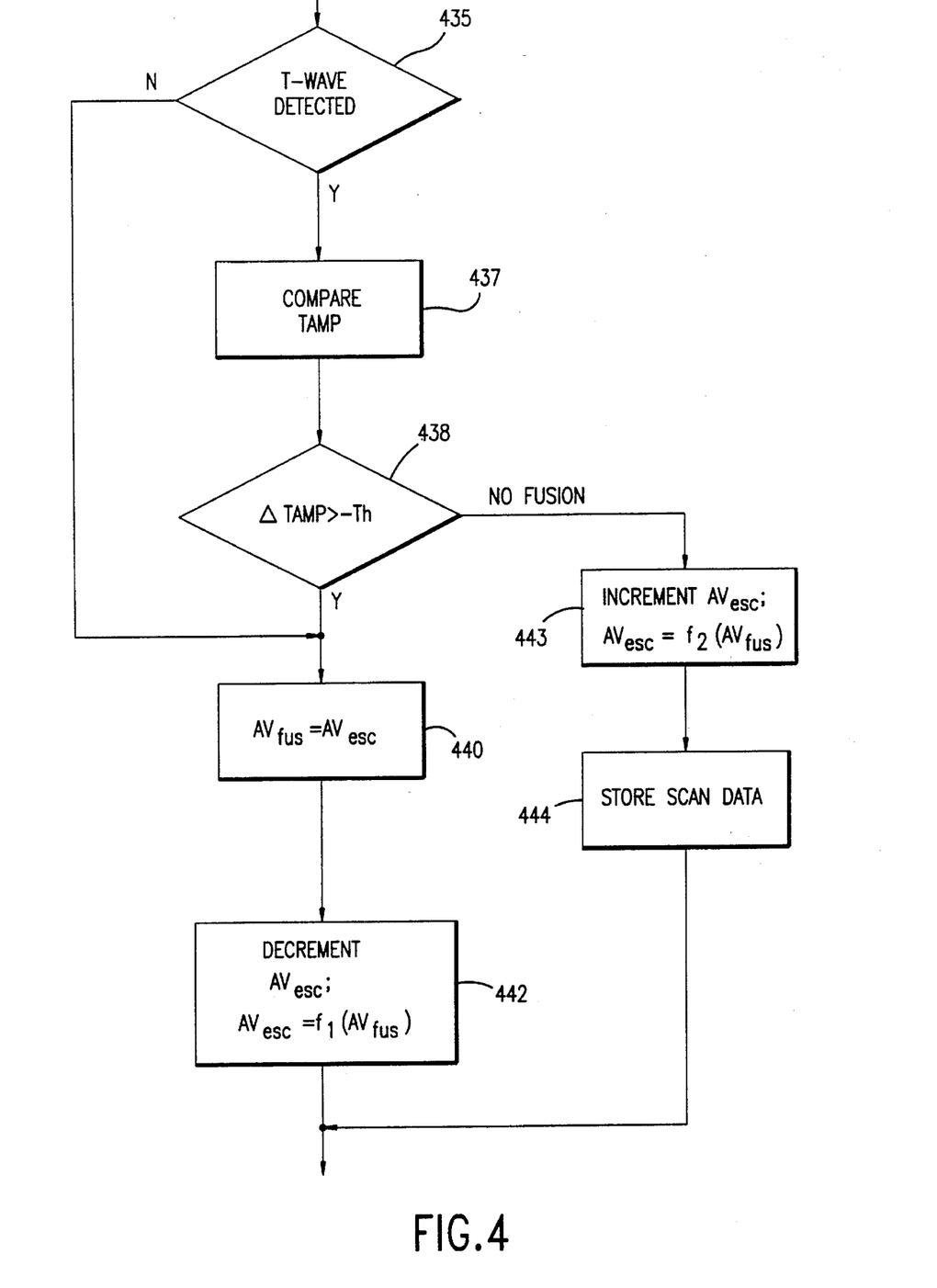
FIG. 4 is a generalized flow diagram for carrying out the adjust step in accordance with the preferred embodiment of this invention.

Referring now to FIG. 4, there is shown a more detailed flow diagram of the apparatus and method of this invention, corresponding to a first embodiment of blocks 420 and 422 of FIG. 3. In FIG. 4, in order to simplify the discussion, there is no distinction made between SAV and PAV, and only adjustment of $AV_{esc}$ is shown. At 435, the pacemaker monitors the ventricular sense amplifier response, to see if a T-wave has been detected on line 353. If no, i.e., there has been a significant drop in T-wave amplitude, this indicates that the delivered VP resulted in a fusion beat, or at least a near-fusion or quasi-fusion beat. In this case, the routine then branches to block 440, and sets a variable designated $AV_{fus}$ to the current value of $AV_{esc}$ which led to the fusion beat. If a T-wave is detected at 435, the routine proceeds to block 437, determines the amplitude of the T-wave ($T_{amp}$), and compares it to the prior value of $T_{amp}$. The present sensitivity of T-wave sensing amplifiers, such as used in Q-T rate responsive pacemakers made by Vitatron Medical, B.V., assignee of this invention, can be programmed within a range of 0.5–3.0 mV, and comparisons can be made to 0.25 mV. At block 438, the pacemaker compares the change in $T_{amp}$, to see if there has been a decrement greater than a predetermined threshold indicated as $T_h$. This comparison is made because an abrupt and significant drop in T-wave amplitude can reliably indicate the onset of fusion, even though the T-wave is still detected. Thus, in accordance with this embodiment of this invention, criteria for fusion is either a loss of T-wave sensing, or a decrease of the T-wave amplitude greater than $T_h$, e.g., more than 25%. If such an abrupt drop has occurred, the pacemaker adjusts the value of $AV_{fus}$ at 440. It then decrements $AV_{esc}$ at 442. The value of the decrement may be a fixed program value, but more suitably is a value calculated by the pacemaker in accordance with $AV_{fus}$ and the history of $AV_{fus}$, as discussed in more detail hereinbelow. Generally, however, as indicated at 442, it is desirable to adjust $AV_{esc}$ as a first function of $AV_{fus}$, $f_1(AV_{fus})$. Returning to 438, if there has been no sudden drop T-wave amplitude, the routine branches to block 443 and increments $AV_{esc}$, taking the value toward the value corresponding to fusion ($AV_{fus}$). The amount of the increment may vary in accordance with different criteria, as discussed hereinbelow. As seen in FIG. 4, $AV_{esc}$ is generally incremented in accordance with a second function of $AV_{fus}$, $f_2(AV_{fus})$. Thereafter, at 445, data concerning the current scan of $V_{esc}$ is stored for use in changing $f_1$ and/or $f_2$, as discussed below in connection with FIGS. 5B–5E.

As stated above, characteristics of the T-wave other than amplitude can be used to detect the onset of fusion. When $AV_{esc}$ approaches $AV_{fus}$, the frequency characteristics and general morphology of the T-wave change. Accordingly, the invention can be practiced by monitoring one or more characteristics of the T-wave, such as duration, slope, etc. Likewise, the stimulus to evoked R-wave duration, and R-wave morphology, change significantly at fusion, and can be used as a control variable.

Figure 5A:
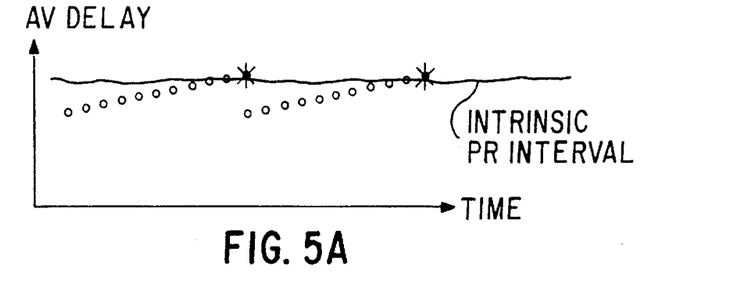
FIG. 5A is a timing diagram which illustrates the results of an algorithm for $AV_{esc}$ control which is based on the detection of ventricular senses.
Figure 5B:
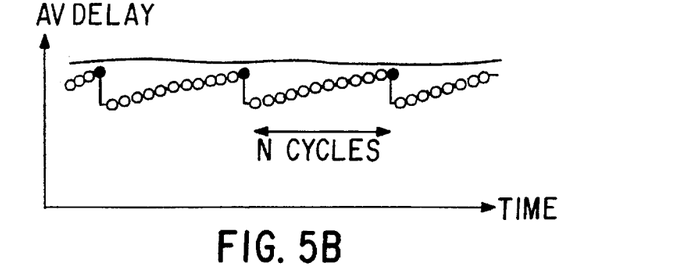
FIGS. 5B–5E are timing diagrams illustrating different search (scan) routines within the scope of this invention.
Figure 5C:
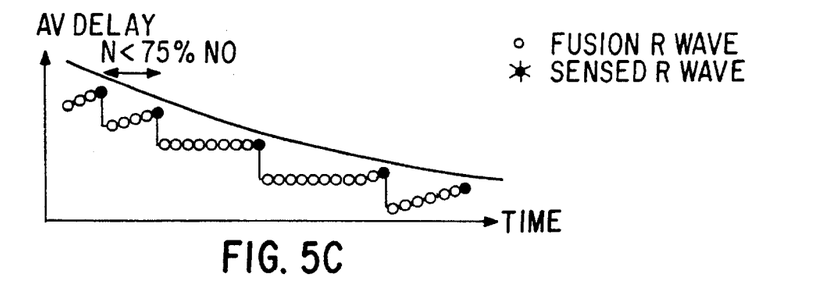

Referring now to FIG. 5A, there is illustrated the result of a pacemaker algorithm which is based on the detection of sensed ventricular events, and thus does not utilize the advantages of this invention. This algorithm scans AV delay through the intrinsic PR interval until a sensed ventricular signal (VS) is obtained, whereafter AV delay is decremented and the search is repeated. As seen, this results in periodic loss of capture, at which point the HOCM patient does not get the benefit of pre-excitation by a pace pulse. By contrast, FIG. 5B, shows a scanning algorithm in accordance with this invention, wherein the pacemaker detects fusion at an AV delay just short of the intrinsic PR interval. FIG. 5B shows a situation with a relatively constant intrinsic PR interval, and each time that fusion is detected by the absence or significant decrease of the T-wave, the algorithm decrements AV by a predetermined amount, e.g., 20 ms. In this embodiment, at block 442, $AV_{esc}$ is simply decremented after a fusion beat by the predetermined amount, which can either be a fixed programmed amount or can be a function of the AV delay at which fusion was found, i.e., $AV_{fus}$. As illustrated in FIG. 5B, for a substantially constant underlying PR interval, the pacemaker increments AV delay through N cycles before detecting fusion. i.e., N=20 for an initial decrement of 20 ms at block 442 and a fixed increment of 1 ms at block 443. However, it is recognized that the intrinsic PR interval will not remain a constant, but will vary with exercise and for other reasons. For example, FIG. 5C shows a situation with a shortening, or decreasing intrinsic interval, e.g., during exercise, and FIG. 5D shows a situation with an increasing intrinsic PR interval, e.g., following cessation of exercise.

In one embodiment of this invention, the pacemaker is programmed to count the scanned cycles during which $AV_{esc}$ is incremented, i.e., count N as part of the operation at block 445. If N remains between 75% and 125% of its nominal value, e.g., between 15 and 25, then the underlying PR interval is considered to be constant. If the underlying PR interval shortens, as illustrated in FIG. 5C, then the number of beats between two fusion detections (N) decreases. For example, if N drops to less than 75% of its nominal value ($N_0$), e.g., 15, this indicates a relatively aggressive shortening and the pacemaker algorithm responds by maintaining a constant AV delay ($AV_{esc}$) for a predetermined number of beats. In this instance, the formula for incrementing $AV_{esc}$ is to hold it constant, i.e., $f_2(AV_{fus})=K$. Normally in this situation, the shortening of the patient's PR interval will cause fusion detection again after less than 20 beats. However, if no fusion is detected after the predetermined number of beats, then progressive AV delay increments, e.g., 1 ms/beat, commence again.

Figure 5D:
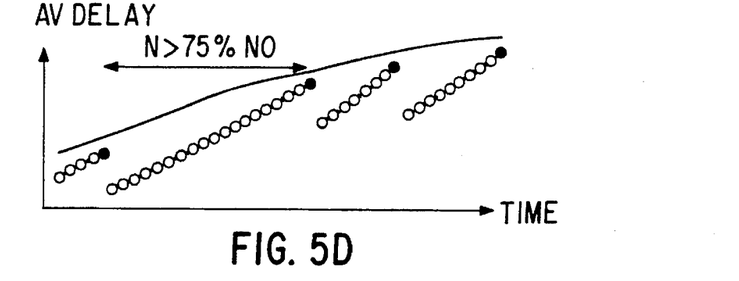

Referring to FIG. 5D, where the patient's intrinsic PR interval is illustrated as lengthening during a recovery from exercise, the number N of cycles between two fusion beats is seen to increase. In accordance with another embodiment, when N exceeds a fixed percentage of nominal N, e.g., $N \geq 1.25 N_0$, the algorithm responds by increasing the step size of the AV increment, e.g., from 1 to 2 ms/beat. When N is detected to again become within 25% of $N_0$, the algorithm reverts to the smaller step size increment. Thus, the technique of counting cycles between fusion beats is a specific embodiment of tracking $AV_{fus}$ and adjusting the $f_2$ function for incrementing $AV_{esc}$ at block 443.

Figure 5E:
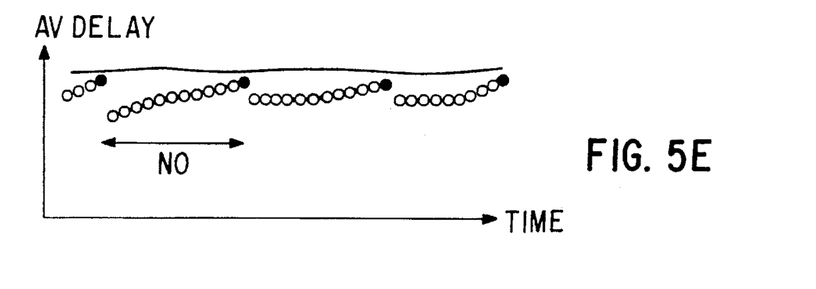

It is to be understood that other alternative programs are possible for adjusting $AV_{esc}$ in order to maximize the AV delay for optimal filling, and yet avoid setting $AV_{esc}$ too long so that capture is occasionally missed. The object of any alternate algorithm is to ensure full capture while also maintaining an optimum AV delay for hemodynamic purposes, even during circumstances in which the patient's underlying rate and intrinsic PR interval is changing. FIG. 5E provides an example of an alternate algorithm, embodying a different $f_1$ for decrementing $AV_{esc}$ following fusion, and a different $f_2$ for incrementing $AV_{fus}$, after fusion. In this example, the $f_1$ function provides for an automatic step reduction of $AV_{esc}$ upon detection of fusion. However, if the patient's underlying PR interval is found to be substantially constant, this step size decrement can be made smaller, and the following cyclical increments in $AV_{esc}$ can likewise be made smaller. For example, after detection of fusion following a scan of N beats, and $0.75 N_0 \leq N \leq 1.25 N_0$, $AV_{esc}$ may be decremented only 10 ms at block 442, instead of 20 ms; following this, $AV_{esc}$ is maintained constant for 50% of the succeeding N beats, and then is incremented at 1 ms per cycle. This would results in a substantially constant value of N between fusion beats, but with the average AV delay being longer and closer to $AV_{fus}$.

This invention provides an improved system and method for a dual chamber pacing therapy for HOCM patients. The invention comprises an improved manner of detecting the upper limit of the range of AV intervals in which the pacemaker is to be paced so as to optimize complete capture of the patient's heart and efficient dual chamber hemodynamics. The invention comprises novel means to detect when the pacemaker AV delay corresponds to a fusion beat, thereby accurately detecting the upper limit of the acceptable range for AV delay without incurring pacemaker cycles where there is no capture due to delivery of a pace pulse. In fact, by the technique of monitoring the sensed T-wave amplitude, the apparatus and method of this invention can detect when a lengthened AV delay reaches a value corresponding to the onset of fusion, providing extra insurance for preventing loss of capture. As used herein, "fusion" or "fusion beat" includes the situation where the evoked response, including the T-wave amplitude, has changed sufficiently to indicate some characteristics of fusion, or near-fusion. The invention also provides an algorithm for optimizing the range of $AV_{esc}$ variation as function of the detected fusion interval, $AV_{fus}$, which is used as the high limit of the pacemakers $AV_{esc}$ range.

What is claimed is:

1. A dual chamber pacemaker system, having atrial sense means for sensing atrial signals from a patient, ventricular sense means for sensing ventricular signals from a patient, ventricular pace means for generating and delivering ventricular pace pulses to said patient's right ventricle, and sync control means for controlling said pace means to generate and deliver a ventricular pace pulse at a controlled AV escape interval following a sensed atrial signal, said sync control means having $AV_{esc}$ means for setting said AV escape interval, said $AV_{esc}$ means comprising:

fusion means for detecting the occurrence of a fusion beat and the value $AV_{fus}$ of the AV escape interval corresponding to which a said fusion beat is detected, and program means for changing said AV escape interval so as to maintain said $AV_{esc}$ within a small range of values no greater than said value of $AV_{fus}$, whereby pace pulses are delivered at an AV escape interval no greater than said $AV_{fus}$.

2. The pacemaker system as described in claim 1, wherein said program means has decrement means for decrementing said AV escape interval for the next ventricular pace pulse following a detected fusion beat.

3. The pacemaker system as described in claim 2, wherein said program means has means for increasing said AV escape interval by constant increments following a said next ventricular pace pulse.

4. The pacemaker system as described in claim 1, wherein said program means changes said AV escape interval so as to permit detection of a fusion beat without extending the AV escape interval to a value greater than $AV_{fus}$, thereby avoiding a ventricular sense before timeout of a said AV escape interval.

5. A dual chamber pacemaker system, having atrial sense means for sensing atrial signals from a patient, ventricular sense means for sensing ventricular signals from a patient, ventricular pace means for generating and delivering ventricular pace pulses to said patient's right ventricle, and sync control means for controlling said pace means to generate and deliver a ventricular pace pulse at a controlled AV escape interval following a sensed atrial signal, said sync control means having $AV_{esc}$ means for setting said AV escape interval, said $AV_{esc}$ means comprising fusion means for detecting the occurrence of a fusion beat and the value $AV_{fus}$ of the AV escape interval corresponding to which a said fusion beat is detected, storing means for storing said value of $AV_{fus}$ and program means for changing said AV escape interval as a function of said stored $AV_{fus}$ value.

6. The pacemaker system as described in claim 5 wherein said fusion means comprises detection means for detecting T-waves following delivery of ventricular pace pulses, and first determining means for determining a fusion beat when no T-wave is detected following a delivered ventricular pace pulse.

7. The pacemaker system as described in claim 5, wherein said fusion means comprises T-wave detection means for detecting a T-wave in response to a delivered ventricular pace pulse, amplitude means for determining the amplitude of a said detected T-wave, and second determining means for determining a fusion beat as a function of said detected T-wave amplitude.

8. The pacemaker system as described in claim 5, wherein said fusion means comprises T-wave sensing means for sensing T-waves following delivery of ventricular pace pulses, first means for determining the frequency of detected fusion beats, and wherein said program means adjusts said AV escape interval as a function of said determined frequency.

9. A dual chamber pacemaker having atrial sense means for sensing signals in a patient's atrium, ventricular sense means for sensing signals in said patient's ventricle, ventricular pace means for generating and delivering ventricular pace pulses to the patient's ventricle, and AV control means for controlling said pace means to generate and deliver a ventricular pace pulse at a controlled AV escape interval following a sensed atrial signal, comprising:

monitoring means for monitoring at least one of said signals sensed in said patient's atrium and said patient's ventricle and detecting therefrom when a delivered pace pulse causes a fusion beat;

fusion means for determining the AV escape interval $AV_{fus}$ corresponding to a detected fusion beat; and adjusting means for adjusting said AV escape interval to a value less than said $AV_{fus}$.

10. The dual chamber pacemaker a described in claim 9, wherein said monitoring means comprises means for monitoring T-wave amplitude, and evaluation means for evaluating when said T-wave amplitude indicates the occurrence of fusion.

11. The dual chamber pacemaker a described in claim 9, wherein said monitoring means comprises means for monitoring T-wave morphology, and evaluation means for evaluating when said T-wave morphology indicates the occurrence of fusion.

12. The dual chamber pacemaker as described in claim 9, wherein said adjusting means comprises means for determining the number of paced ventricular beats between fusion beats, and for adjusting said AV escape interval as a function of said number.

13. The dual chamber pacemaker as described in claim 9, wherein said adjusting means comprises program means for varying said AV escape interval within a range below $AV_{fus}$ and as a function of $AV_{fus}$.

14. The dual chamber pacemaker as described in claim 9, wherein said adjusting means has means for decrementing said AV escape interval for at least the next pacemaker cycle following detecting that a delivered pace pulse has caused a fusion beat, and means for adjusting said decrement as a function of the determined $AV_{fus}$.

15. A method of therapy for treating a patient with HOCM, said method utilizing a dual chamber pacemaker having atrial sense means for sensing atrial signals form a patient, ventricular sense means for sensing ventricular signals from a patient, ventricular pace means for generating and delivering ventricular pace pulses to said patient's right ventricle, and sync control means for controlling said pace means to generate and deliver a ventricular pace pulse at a controlled AV escape interval following a sensed atrial signal, said sync control means having $AV_{esc}$ means for setting said AV escape interval, said method comprising:

pacing said patient's right ventricle with an AV escape interval shorter than the patient's intrinsic PR conduction duration so as to provide complete capture with delivered pace pulses, detecting the occurrence of fusion beats by monitoring evoked T-waves and determining when the T-wave amplitude drops to a level indicative of a fusion, and following a said detected fusion beat adjusting said AV escape interval to a value less than the value which resulted in a fusion beat.

16. The method in accordance with claim 15, comprising determining the frequency of evoked fusion beats, and thereafter adjusting said AV escape interval as a function of said detected frequency.

17. The method as described in claim 15, comprising detecting a fusion beat by sensing patient T-waves and monitoring at least one characteristic of said sensed T-waves.

18. The method as described in claim 15, comprising incrementing said AV escape interval during succeeding pacing cycles so that said AV escape interval is increased toward the value where the last fusion beat occurred.

* * * * *

UNITED STATES PATENT AND TRADEMARK OFFICE
CERTIFICATE OF CORRECTION

PATENT NO. : 5,534,016
DATED : July 9, 1996
INVENTOR(S) : Willem Boute

It is certified that error appears in the above-indentified patent and that said Letters Patent is hereby corrected as shown below:

Col. 1, 19, "septurn" should be --septum--.

Col. 8, line 11, "dam" should be --data--

Col. 10, line 54, "1 ins" should be --1 ms--.

Signed and Sealed this

Twenty-fifth Day of November, 1997

Attest:

BRUCE LEHMAN

*Attesting Officer*          *Commissioner of Patents and Trademarks*